United States Patent
Lee et al.

(10) Patent No.: US 10,865,212 B2
(45) Date of Patent: Dec. 15, 2020

(54) INTERMEDIATE FOR PREPARING ERIBULIN MESYLATE AND PROCESS FOR PREPARING THE SAME

(71) Applicant: YONSUNG FINE CHEMICAL CO., LTD., Hwaseong-si (KR)

(72) Inventors: Hyoseon Lee, Bucheon-si (KR); Hyunik Shin, Suwon-si (KR); Keeyoung Lee, Seoul (KR); Changyoung Oh, Seongnam-si (KR)

(73) Assignee: YONSUNG FINE CHEMICAL CO.. LTD., Hwaseong-si (KR)

( * ) Notice: Subject to any disclaimer, the term of this patent is extended or adjusted under 35 U.S.C. 154(b) by 0 days.

(21) Appl. No.: 16/475,171

(22) PCT Filed: Jan. 2, 2018

(86) PCT No.: PCT/KR2018/000043
§ 371 (c)(1),
(2) Date: Jul. 1, 2019

(87) PCT Pub. No.: WO2018/124847
PCT Pub. Date: Jul. 5, 2018

(65) Prior Publication Data
US 2019/0337964 A1 Nov. 7, 2019

(30) Foreign Application Priority Data

Jan. 2, 2017 (KR) .................... 10-2017-0000380
Dec. 14, 2017 (KR) .................... 10-2017-0172077

(51) Int. Cl.
*C07D 493/04* (2006.01)
*C07D 309/10* (2006.01)

(52) U.S. Cl.
CPC ......... *C07D 493/04* (2013.01); *C07D 309/10* (2013.01)

(58) Field of Classification Search
CPC ............. C07D 493/04; C07D 309/10

USPC ........................................... 549/396
See application file for complete search history.

(56) References Cited

U.S. PATENT DOCUMENTS

| 6,214,865 B1 | 4/2001 | Littlefield et al. |
| 2007/0244187 A1 | 10/2007 | Austad et al. |
| 2015/0005343 A1 | 1/2015 | Nomoto et al. |
| 2017/0158705 A1 | 6/2017 | Zhang et al. |

FOREIGN PATENT DOCUMENTS

| JP | 2002-518384 | 6/2002 |
| JP | 2008-501715 | 1/2008 |
| KR | 10-2007-0030260 A | 3/2007 |
| KR | 10-2016-0023816 A | 3/2016 |
| KR | 10-2017-0030534 A | 3/2017 |
| KR | 10-1880939 B1 | 8/2018 |
| WO | 2005/118565 | 12/2005 |
| WO | 2016/004805 A1 | 1/2016 |

OTHER PUBLICATIONS

Duan et al., Tetrahedron Letters, (1993) vol. 34, No. 47, pp. 7541-7544.*
Melvin J. Yu et al., "From micrograms to grams: scale-up synthesis of eribulin mesylate," Natural Product Reports, 2013, pp. 1158-1164, vol. 30.
Charles E. Chase et al., "Process Development of Halaven®: Synthesis of the C1-C13 Fragment from D-(−)-Gulono-1,4-lactone," SYNLETT, 2013, pp. 323-326 (5 pages), vol. 24.
Dean P. Stamos et al., "Synthetic Studies on Halichondrins: A Practical Synthesis of the C.1-C.13 Segment," Tetrahedron Letter, 1996, pp. 8643-8646, vol. 37, No. 48.
International Search Report of PCT/KR2018/000043 dated Apr. 16, 2018.

* cited by examiner

*Primary Examiner* — Niloofar Rahmani
(74) *Attorney, Agent, or Firm* — Sughrue Mion, PLLC

(57) ABSTRACT

The present invention relates to a process for preparing an intermediate for the preparation of eribulin mesylate with high yields, and an intermediate therefor.

9 Claims, No Drawings

INTERMEDIATE FOR PREPARING ERIBULIN MESYLATE AND PROCESS FOR PREPARING THE SAME

CROSS REFERENCE TO RELATED APPLICATIONS

This application is a National Stage of International Application No. PCT/KR2018/000043 filed Jan. 2, 2018, claiming priority based on Korean Patent Application No. 10-2017-0000380 filed Jan. 2, 2017 and Korean Patent Application No. 10-2017-0172077 filed Dec. 14, 2017.

TECHNICAL FIELD

The present invention relates to an intermediate for the preparation of eribulin mesylate and a process for preparing the same.

BACKGROUND ART

Eribulin mesylate represented by the following formula (1) is an active pharmaceutical ingredient (API) of Halaven which is a medicine for breast cancer.

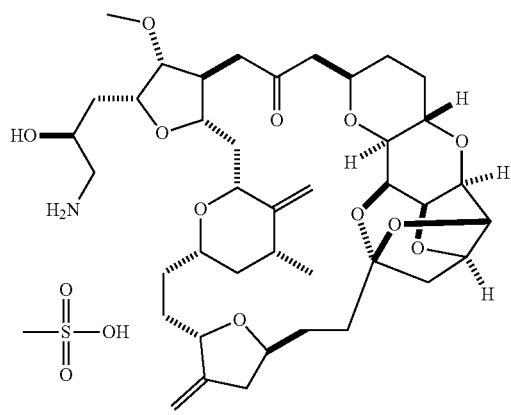

(1)

U.S. Pat. No. 6,214,865 discloses a process for preparing eribulin mesylate of formula (1) using the compound of the following formula (2) as a key intermediate, as shown in the following reaction scheme 1.

[Reaction Scheme 1]

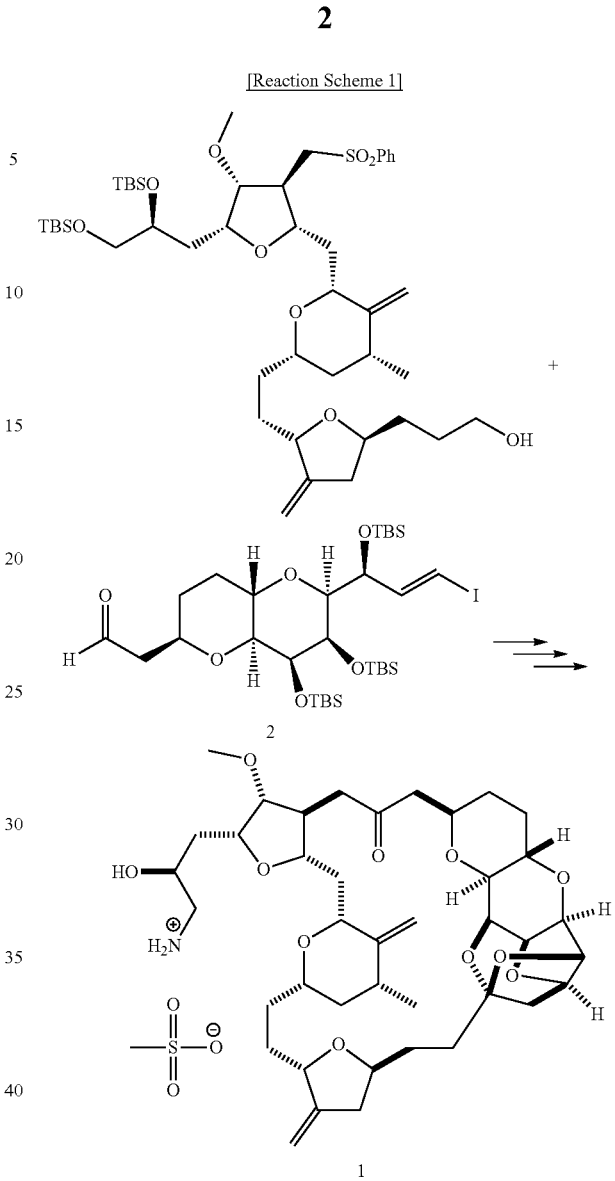

Also, Tetrahedron Letter 1996, 37, 8643-8646 describes a process for preparing the compound of formula (2) using deacetylation, olefin conjugation and oxy-Michael addition using L-mannonic acid γ-lactone as a starting material, as shown in the following reaction scheme 2.

[Reaction Scheme 2]

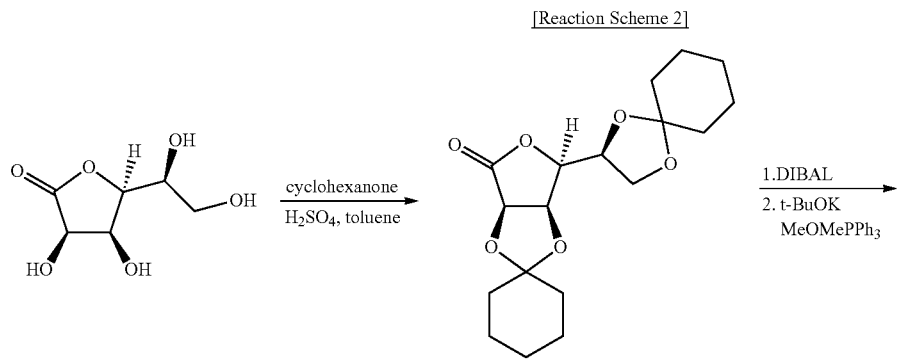

-continued
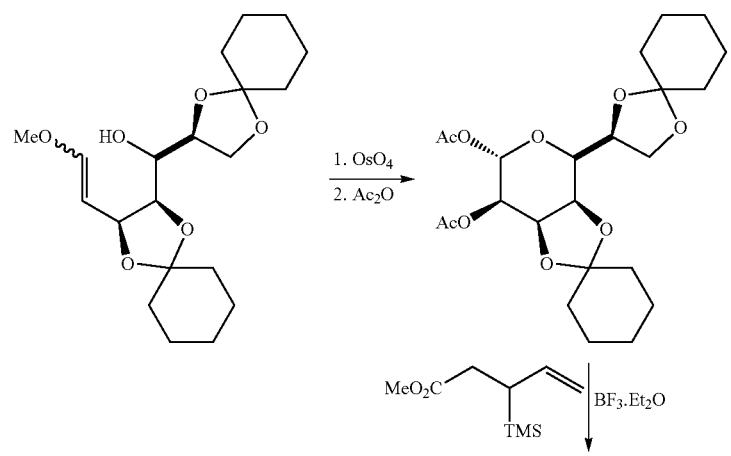
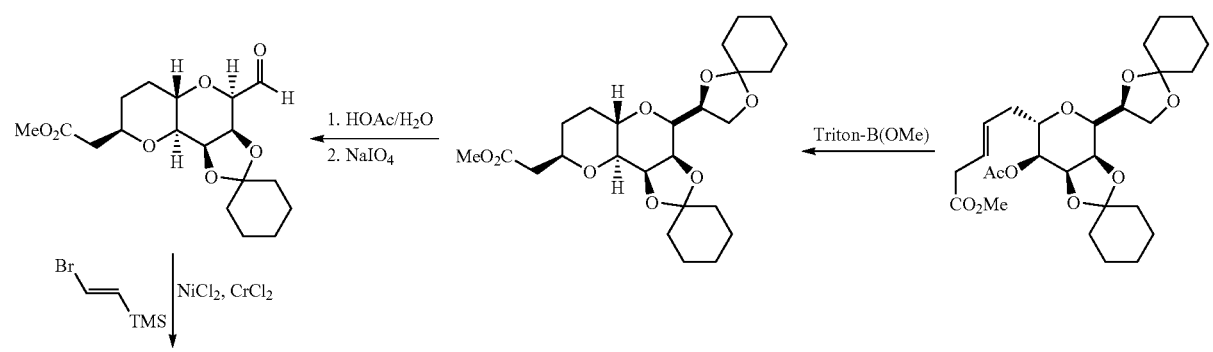
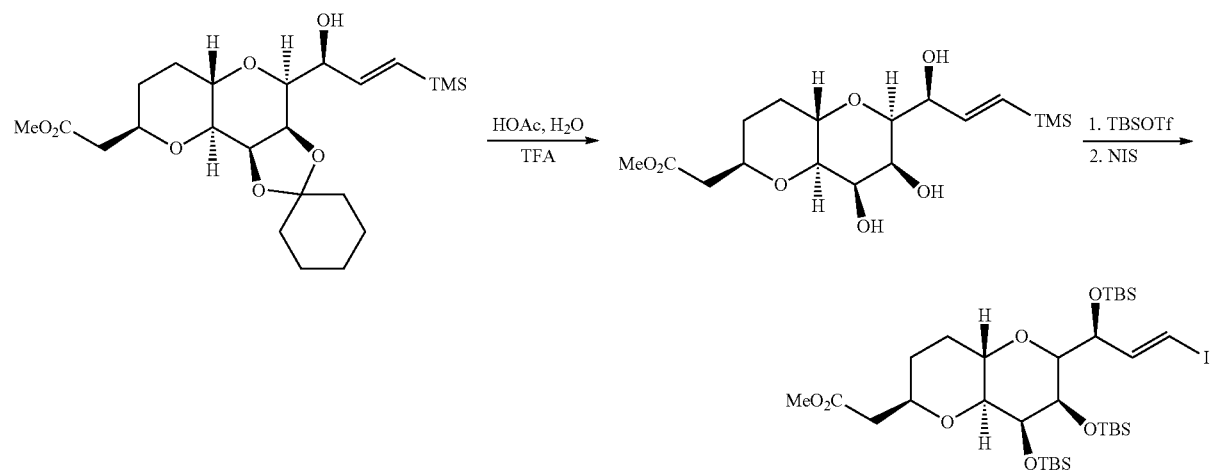

However, the prior processes are sensitive to reaction conditions and comprise long pathway, and thus they have problems that the yield of the compound of formula (2) is lowered.

DISCLOSURE

Technical Problem

An object of the present invention is to provide an intermediate for preparing the compound of formula (2) with high yields, which is a key intermediate for the preparation of eribulin mesylate.

Another object of the present invention is to provide a process for preparing the above intermediate.

Still another object of the present invention is to provide an intermediate used in the above preparation process.

Technical Solution

One embodiment of the present invention relates to a compound of the following formula (3) which is an intermediate for preparing the compound of formula (2) which is a key intermediate for the preparation of eribulin mesylate:

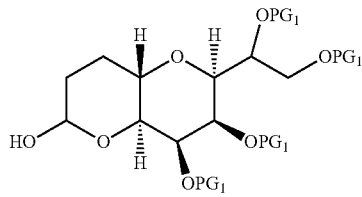

(3)

wherein, $PG_1$ represents a diol protecting group forming a 5-membered heterocycle by combining each other.

One embodiment of the present invention relates to a process for preparing the compound of formula (3), which comprises the steps of:

(i) subjecting a compound of the following formula (4) to Wittig reaction to obtain a compound of the following formula (5);
(ii) selectively deprotecting a $PG_2$ group of the compound of the following formula (5) to obtain a compound of the following formula (6);
(iii) subjecting the compound of the following formula (6) to cyclization to obtain a compound of the following formula (7);
(iv) subjecting the compound of the following formula (7) to hydrogenation to obtain a compound of the following formula (8); and
(v) reducing an ester group of the compound of the following formula (8):

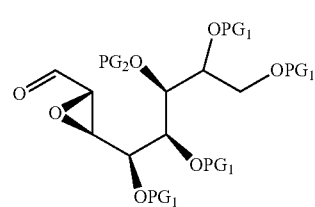

(4)

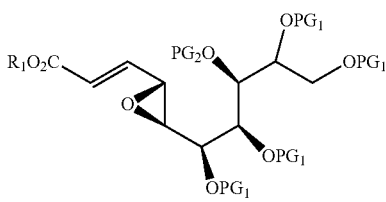

(5)

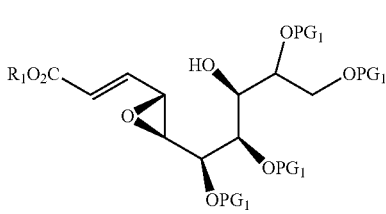

(6)

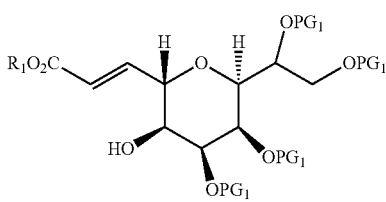

(7)

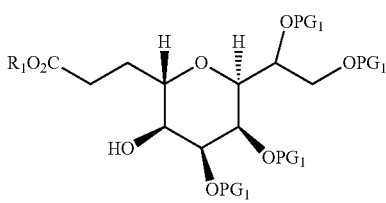

(8)

wherein, $PG_1$ represents a diol protecting group forming a 5-membered heterocycle by combining each other, $PG_2$ represents a silyl protecting group, and $R_1$ represents hydrogen or a $C_1$-$C_6$ alkyl group.

The term "diol protecting group" as used herein may be a diol protecting group derived from a cycloketone such as cyclopentanone, cyclohexanone and cycloheptanone; or a cycloketal such as 1,1-dimethoxycyclopentane, 1,1-dimethoxycyclohexane and 1,1-dimethoxycycloheptane.

The term "$C_1$-$C_6$ alkyl group" as used herein means a linear or branched hydrocarbon having 1 to 6 carbon atoms, which includes methyl, ethyl, n-propyl, i-propyl, n-butyl, i-butyl, t-butyl, n-pentyl, n-hexyl and the like, but is not limited thereto.

The term "silyl protecting group" as used herein includes trimethylsilyl (TMS), triethylsilyl (TES), t-butyldimethylsilyl (TBS), t-butyldiphenylsilyl (TBDPS) and the like, but is not limited thereto.

Hereinafter, the preparation process according to one embodiment of the present invention is described in more detail referring to the following reaction scheme 3. The process depicted in the following reaction scheme 3 represents merely a typical example, and various changes may be made to reagents and reaction conditions without limitation.

[Reaction Scheme 3]

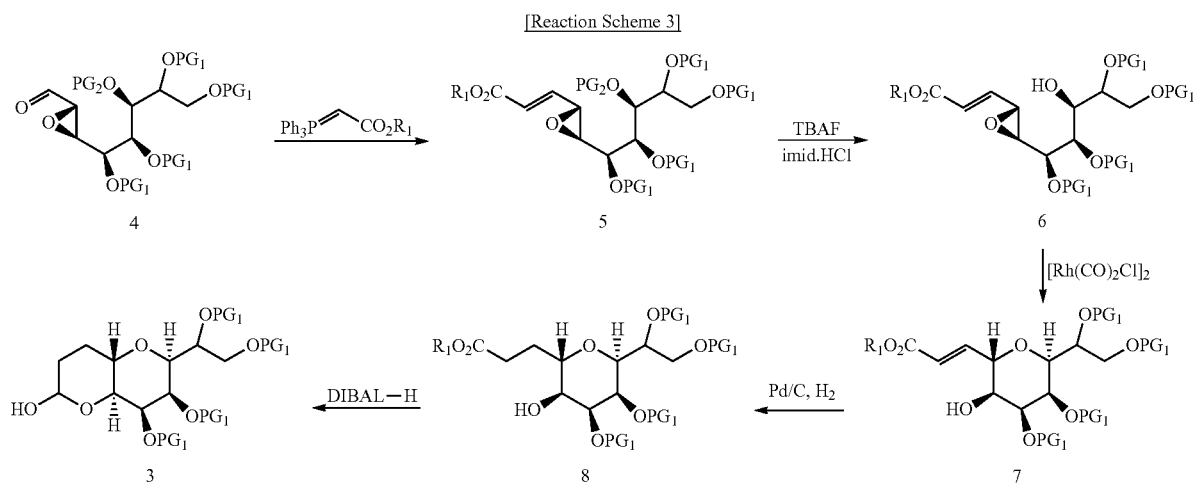

Step 1: Synthesis of Compound of Formula (5)

The compound of formula (5) can be obtained by subjecting the compound of formula (4) to Wittig reaction.

The Wittig reaction may be carried out using (methoxycarbonylmethylene)triphenylphosphorane, (ethoxycarbonylmethylene)triphenylphosphorane and the like.

As a reaction solvent, methylenechloride, tetrahydrofuran, toluene, etc. may be used. Particularly, methylenechloride is preferred.

The reaction is preferably performed at room temperature.

Step 2: Synthesis of Compound of Formula (6)

The compound of formula (6) can be obtained by selectively deprotecting the $PG_2$ group of the compound of formula (5).

The deprotection may be carried out using a mixture of a fluoride (F) compound and a buffer.

The fluoride compound may be preferably tetra-n-butylammonium fluoride (TBAF), and the buffer may be preferably imidazole hydrochloride.

As the reaction solvent, tetrahydrofuran, ether, acetone, etc. may be used. Particularly, tetrahydrofuran is preferred.

The reaction is preferably performed at room temperature.

Step 3: Synthesis of Compound of Formula (7)

The compound of formula (7) can be obtained by subjecting the compound of formula (6) to cyclization.

The cyclization may be carried out in the presence of a catalyst such as pyridinium paratoluenesulfonate (PPTS), camphorsulfonic acid (CSA) and di-µ-chloro-tetracarbonyldirhodium(I). Particularly, di-µ-chloro-tetracarbonyldirhodium(I) is preferred.

As a reaction solvent, methylenechloride, chloroform, tetrahydrofuran, etc. may be used. Particularly, tetrahydrofuran is preferred.

The reaction is preferably performed at room temperature.

Step 4: Synthesis of Compound of Formula (8)

The compound of formula (8) can be obtained by subjecting the C—C double bond of the compound of formula (7) to hydrogenation.

The hydrogenation may be carried out in the presence of Pd/C.

As a reaction solvent, methanol, ethanol, ethylacetate, etc. may be used. Particularly, ethylacetate is preferred.

The reaction is preferably performed at room temperature.

Step 5: Synthesis of Compound of Formula (3)

The compound of formula (3) can be obtained by reducing the ester group of the compound of formula (8).

The reduction may be carried out using lithium aluminum tetrahydride, sodium bis(2-methoxyethoxy)aluminum dihydride, diisobutylaluminum hydride (DIBAL-H), etc. Particularly, diisobutylaluminum hydride is preferred.

As a reaction solvent, methylenechloride, toluene, tetrahydrofuran, etc. may be used. Particularly, toluene is preferred.

The reaction is preferably performed at the temperature of −65° C. or lower.

One embodiment of the present invention relates to a compound of the following formula (7) which is an intermediate for preparing the compound of formula (3):

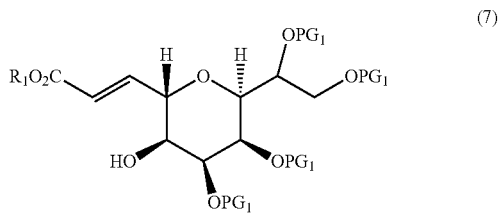

(7)

wherein, $PG_1$ represents a diol protecting group forming a 5-membered heterocycle by combining each other, and $R_1$ represents hydrogen or a $C_1$-$C_6$ alkyl group.

One embodiment of the present invention relates to a process for preparing the compound of formula (7), which comprises the steps of:

(i) subjecting a compound of the following formula (4) to Wittig reaction to obtain a compound of the following formula (5);

(ii) selectively deprotecting a $PG_2$ group of the compound of the following formula (5) to obtain a compound of the following formula (6); and (iii) subjecting the compound of the following formula (6) to cyclization:

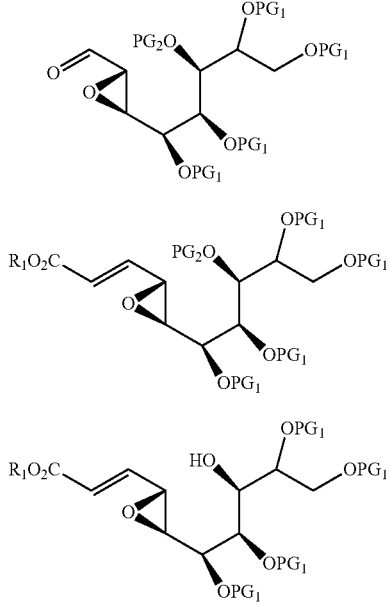

wherein,
PG$_1$ represents a diol protecting group forming a 5-membered heterocycle by combining each other,
PG$_2$ represents a silyl protecting group, and
R$_1$ represents hydrogen or a C$_1$-C$_6$ alkyl group.

The process for preparing the compound of formula (7) includes the same steps 1 to 3 as in the above process for preparing the compound of formula (3), and thus a detailed description thereof will be omitted.

One embodiment of the present invention relates to a process for preparing a compound of the following formula (2) which is a key intermediate for the preparation of eribulin mesylate, which comprises the steps of:

(vi) subjecting a compound of the following formula (3) to Horner-Wadsworth-Emmons reaction to obtain a compound of the following formula (9);
(vii) selectively deprotecting a primary hydroxyl protecting group of the compound of the following formula (9) to obtain a compound of the following formula (10);
(viii) oxidizing the compound of the following formula (10) to obtain a compound of the following formula (11);
(ix) subjecting the compound of the following formula (11) to Nozaki-Hiyama-Kishi reaction with (2-bromovinyl)trimethylsilane to obtain a compound of the following formula (12);
(x) deprotecting a secondary hydroxyl protecting group of the compound of the following formula (12) to obtain a compound of the following formula (13);
(xi) protecting a hydroxyl group of the compound of the following formula (13) to obtain a compound of the following formula (14);
(xii) subjecting a trimethylsilyl group of the compound of the following formula (14) to substitution with an iodide to obtain a compound of the following formula (15); and
(xiii) reducing an ester group of the compound of the following formula (15):

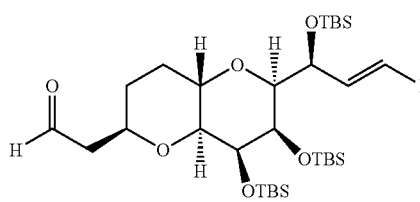

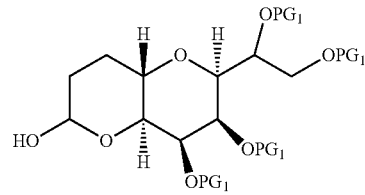

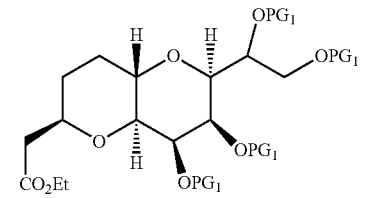

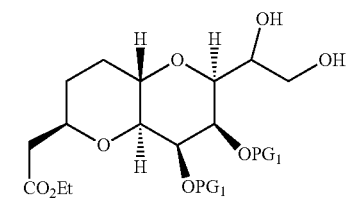

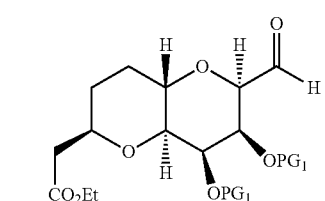

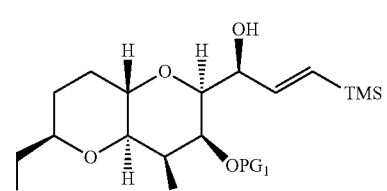

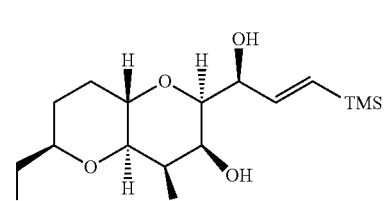

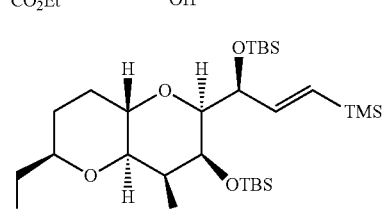

-continued

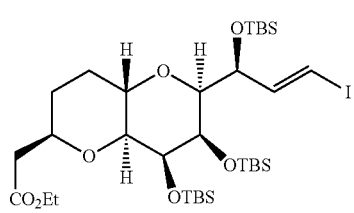

(15)

wherein,
PG$_1$ represents a diol protecting group forming a 5-membered heterocycle by combining each other,
TMS represents trimethylsilyl, and
TBS represents t-butyldimethylsilyl.

Hereinafter, the preparation process according to one embodiment of the present invention is described in more detail referring to the following reaction scheme 4. The process depicted in the following reaction scheme 4 represents merely a typical example, and various changes may be made to reagents and reaction conditions without limitation.

As the reaction solvent, methylene chloride, toluene, tetrahydrofuran, etc. may be used. Particularly, tetrahydrofuran is preferred.

The reaction is preferably performed at room temperature.

Step 7: Synthesis of Compound of Formula (10)

The compound of formula (10) can be obtained by selectively deprotecting the primary hydroxyl protecting group of the compound of formula (9).

The deprotection may be carried out in the presence of an acid.

As the acid, hydrochloric acid, hydrosulfuric acid, acetic acid, etc. may be used. Particularly, acetic acid may be used.

The reaction is preferably performed at the temperature of about 30 to 35° C.

Step 8: Synthesis of Compound of Formula (11)

The compound of formula (11) can be obtained by oxidizing the compound of formula (10).

The oxidation may be carried out using sodium periodate (NaIO$_4$), lead tetraacetate (Pb(C$_2$H$_3$O$_2$)$_4$), etc. Particularly, sodium periodate is preferred.

As the reaction solvent, a mixture of a polar solvent and water is preferred. Specific examples of the polar solvent

[Reaction Scheme 4]

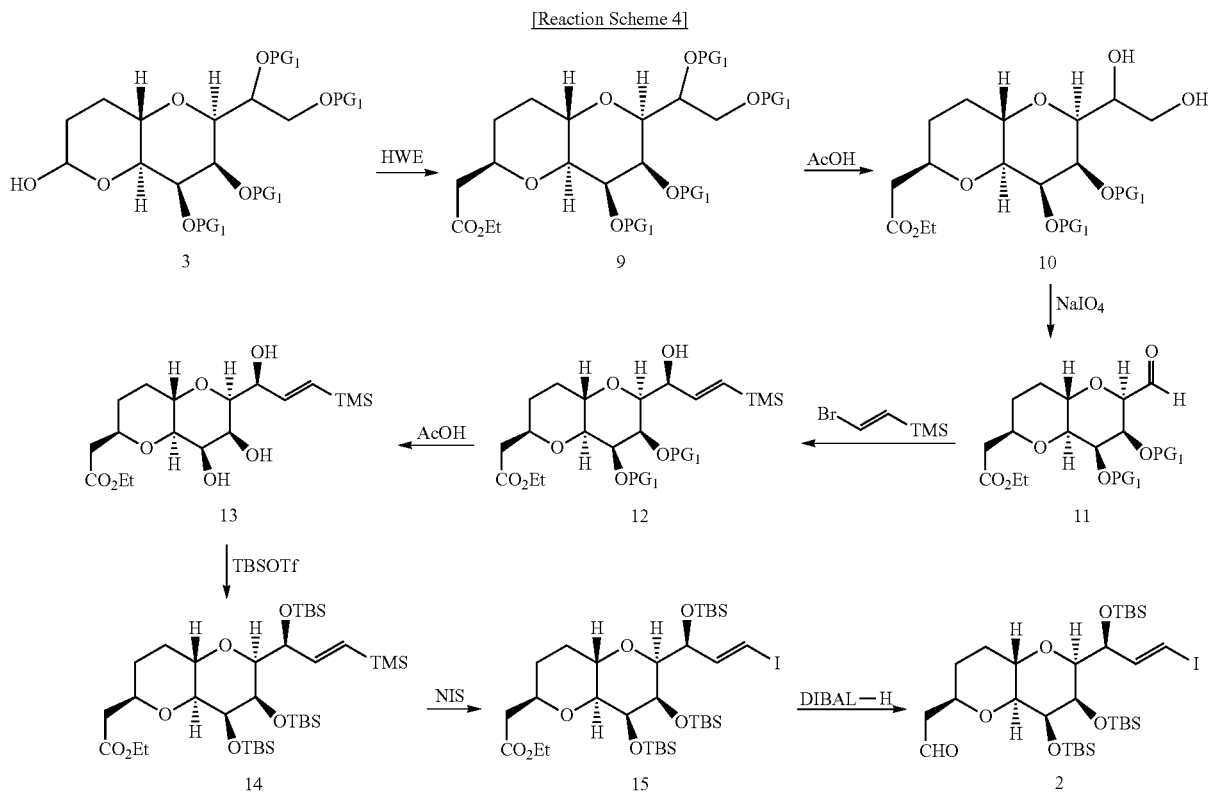

Step 6: Synthesis of Compound of Formula (9)

The compound of formula (9) can be obtained by subjecting the compound of formula (3) to Horner-Wadsworth-Emmons (HWE) reaction.

The Horner-Wadsworth-Emmons reaction may be carried out using triethyl phosphonoacetate, trimethyl phosphonoacetate and the like in the presence of a base.

As the base, lithium bis(trimethylsilyl)amide (LiHMDS), sodium bis(trimethylsilyl)amide (NaHMDS), potassium tert-butoxide (t-BuOK), etc. may be used. Particularly, potassium tert-butoxide may be used.

may include ethylacetate, tetrahydrofuran, toluene, etc. Particularly, ethylacetate is preferred.

The reaction is preferably performed at room temperature.

Step 9: Synthesis of Compound of Formula (12)

The compound of formula (12) can be obtained by subjecting the compound of formula (11) to Nozaki-Hiyama-Kishi (NHK) reaction with (2-bromovinyl)trimethylsilane.

The Nozaki-Hiyama-Kishi reaction may be carried out in the presence of chromium(II) chloride and nickel(II) chloride.

As the reaction solvent, acetonitrile, methylenechloride, dimethyl sulfoxide, etc. may be used. Particularly, a mixture of acetonitrile and dimethyl sulfoxide is preferred.

The reaction is preferably performed at room temperature.

Step 10: Synthesis of Compound of Formula (13)

The compound of formula (13) can be obtained by deprotecting the secondary hydroxyl protecting group of the compound of formula (12).

The deprotection may be carried out in the presence of an acid.

As the acid, hydrochloric acid, hydrosulfuric acid, acetic acid, etc. may be used. Particularly, acetic acid may be used.

The reaction is preferably performed at the temperature of about 90 to 100V.

Step 11: Synthesis of Compound of Formula (14)

The compound of formula (14) can be obtained by protecting the hydroxyl groups of the compound of formula (13).

The protection may be carried out by reacting the compound of formula with t-butyldimethylsilyl trifluoromethanesulfonate under a basic condition.

As the base, triethylamine, 4-dimethylaminopyridine, imidazole, 2,6-lutidine, etc, may be used. Particularly, 2,6-lutidine is preferred.

As the reaction solvent, methylene chloride, chloroform, methyl t-butyl ether (MTBE), etc, may be used. Particularly, methyl t-butyl ether is preferred.

The reaction is preferably performed at room temperature.

Step 12: Synthesis of Compound of Formula (15)

The compound of formula (15) can be obtained by subjecting the trimethylsilyl group of the compound of formula (14) to substitution with an iodide.

The substitution may be carried out using N-iodosuccinimide (NIS), iodine, etc.

Also, the substitution may be carried out in the presence of t-butyldimethylsilyl chloride (TBSCl).

As the reaction solvent, a mixture of acetonitrile and toluene is preferred.

The reaction is preferably performed at the temperature of about 30° C.

Step 13: Synthesis of Compound of Formula (2)

The compound of formula (2) can be obtained by reducing the ester group of the compound of formula (15).

The reduction may be carried out using lithium aluminum tetrahydride, sodium bis(2-methoxyethoxy)aluminum dihydride, diisobutylaluminum hydride (DIBAL-H), etc. Particularly, diisobutylaluminum hydride is preferred.

As the reaction solvent, methylene chloride, toluene, tetrahydrofuran, etc. may be used. Particularly, toluene is preferred.

The reaction is preferably performed at the temperature of −65° C. or lower.

Advantageous Effects

In accordance with the preparation process of the present invention, the compound of formula (2) which is a key intermediate for the preparation of eribulin mesylate can be prepared with high yields.

BEST MODE

The present invention will be described below in more detail by following examples. It will be obvious to those skilled in the art that these examples are merely described for illustration of the present invention and the scope of the present invention is not limited thereto.

Example 1: Synthesis of Compound of Formula (5a)

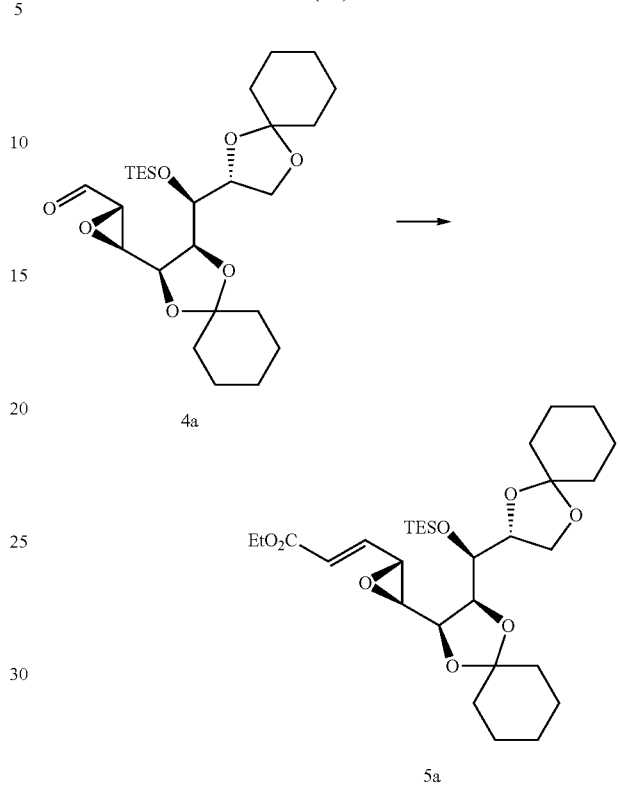

(Ethoxycarbonylmethylene)triphenylphosphorane (52.39 g) was added to the compound of formula (4a) (52 g) dissolved in methylene chloride (0.5 L), followed by stirring for about 2 hours. After the completion of the reaction was confirmed, the resulting solution was concentrated. The resulting residue was subjected to chromatography (ethyl acetate:n-hexane=1:5) to give the compound of formula 5a) (46.6 g, 82%)

$^1$H NMR (300 MHz, CDCl$_3$, δ ppm): 6.66 (dd, J=15.7, 7.2 Hz, 1H). 6.17 (dd, J=15.7, 0.5 Hz, 1H). 4.17-4.30 (m, 2H), 3.99-4.04 (m, 2H), 3.88-3.93 (m, 1H), 3.79 (dd, J=7.7, 5.5 Hz, 1H), 3.43 (dd, J=7.1, 1.5 Hz, 1H), 3.10 (dd, J=7.7, 2.0 Hz, 1H), 1.37-1.67 (m, 23H), 0.93-1.00 (m, 9H), 0.61-0.77 (m, 6H).

Example 2: Synthesis of Compound of Formula (6a)

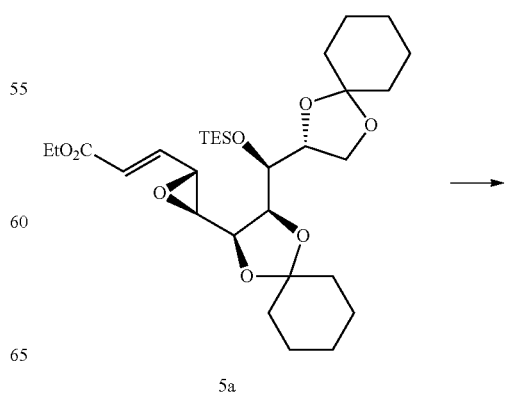

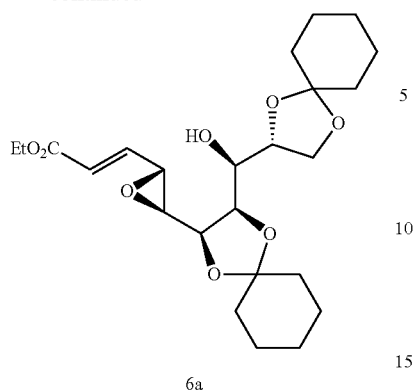

6a

The compound of formula (5a) (44.6 g) was dissolved in tetrahydrofuran (446 mL). A mixture of 1M tetrabutylammonium fluoride (94.5 mL) and imidazole hydrochloride (4.94 g) was added thereto, followed by stirring for about 1.5 hours at the room temperature. After the completion of the reaction was confirmed, water (0.4 L) and ethyl acetate (0.4 L) were added thereto, followed by stirring for 10 minutes. Then, the organic layer was separated, and sodium sulfate was added, followed by filtration and concentration. The resulting residue was subjected to chromatography (ethyl acetate:n-hexane=1:2) to give the compound of formula (6a) (32.5 g, 91%).

$^1$H NMR (300 MHz. CDCl$_3$, δ ppm): 6.68 (dd, J=15.7, 7.1 Hz, 1H). 6.17 (dd, J=15.7, 0.6 Hz, 1H), 4.06-4.29 (m, 5H), 3.78-13.94 (m, 3H), 3.43 (dd, J=7.0, 1.4 Hz, 1H), 3.27 (dd, J=7.8, 1.9 Hz, 1H), 2.49 (d, J=7.6 Hz, 1H), 1.24-1.73 (m, 23H).

Example 3: Synthesis of Compound of Formula (7a)

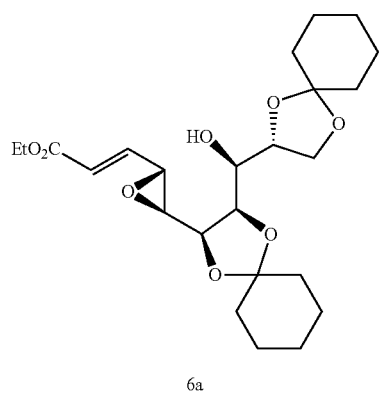

6a

→

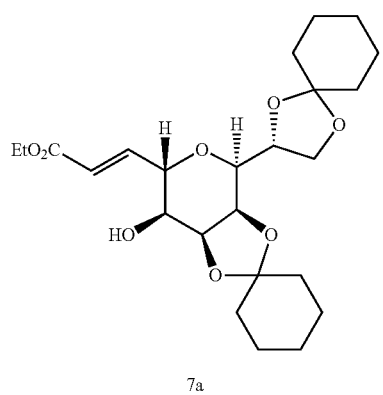

7a

The compound of formula (Ca) (3 g) was dissolved in tetrahydrofuran (230 mL), and di-µ-chloro-tetracarbonyldirhodium(I) (0.99 g) was added thereto, followed by stirring for about 15 hours at room temperature. After the completion of the reaction was confirmed, the resulting solution was concentrated under reduced pressure. The resulting residue was subjected to chromatography (ethyl acetate:n-hexane=1:1) to give the compound of formula (7a) (22.8 g, 78.6%).

$^1$H NMR (300 MHz, CDCl$_3$, δ ppm): 7.12 (dd, J=15.7, 3.2 Hz, 1H), 6.42 (dd, J=15.7, 2.0 Hz, 1H), 4.54-4.58 (m, 1H), 4.41-4.45 (m, 1H), 4.31-4.37 (m, 1H), 4.10-4.26 (m, 4H), 3.77-3.82 (m, 1H), 3.58-3.66 (m, 1H), 3.44 (dd, J=7.9, 1.4 Hz, 1H), 2.20 (d, J=10.3 Hz, 1H), 1.41-1.78 (m, 20H), 1.28 (t, J=7.1 Hz, 3H).

Example 4: Synthesis of Compound of Formula (8a)

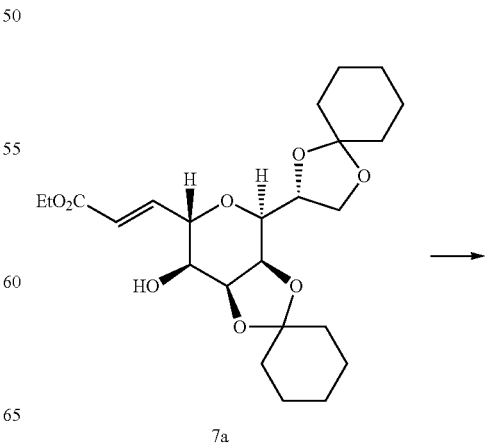

7a

→

-continued

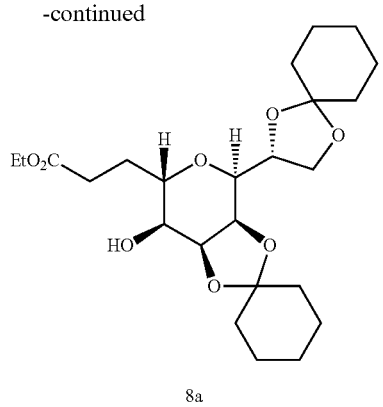

8a

The compound of formula (7a) (22.8 g) was dissolved in ethyl acetate (114 mL), and 10% Pd/C (2.3 g) was added thereto, followed by substitution with hydrogen gas and stirring for about 6 hours. After the completion of the reaction was confirmed, the resulting solution was filtered through cellite. The filtrate was concentrated under reduced pressure, and the obtained compound of formula (8a) (23.5 g, 100%) was used for the following reaction without additional purification.

$^1$H NMR (300 MHz, CDCl$_3$, δ ppm): 4.47-4.50 (m, 1H), 4.23-4.32 (m, 2H), 4.05-4.17 (m, 3H), 3.77-3.86 (m, 2H), 3.49-3.57 (m, 2H), 2.43-2.65 (m, 2H), 2.21-2.25 (m, 1H), 2.02-2.13 (m, 1H), 1.23-1.91 (m, 23H).

Example 5: Synthesis of Compound of Formula (3a)

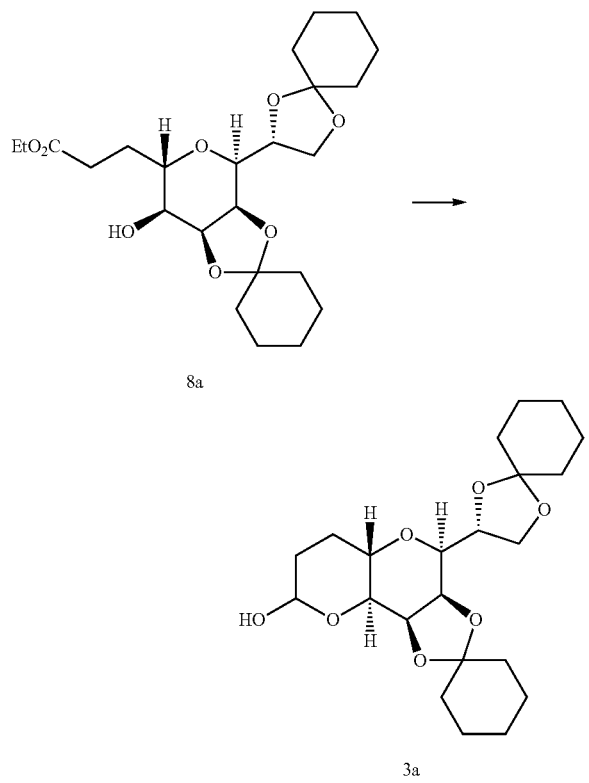

The compound of formula (8a) (23 g) was dissolved in toluene (0.23 L), and cooled to −65° C. or lower. 1.2 M DIBAL-H (105.5 mL) was added dropwise thereto with maintaining the temperature of −60V or lower, followed by stirring for 30 minutes and confirming the completion of the reaction. 20% Potassium sodium tartrate tetrahydrate aqueous solution (0.5 L) was added thereto, with maintaining the temperature of 10° C. or lower, followed by stirring for about 3 hours at room temperature. After the organic layer was separated, the aqueous layer was extracted with ethyl acetate. Sodium sulfate was added to the combined organic layer, followed by filtration and concentration under reduced pressure, to give the compound of formula (3a) (19.6 g, 94.3%).

$^1$H NMR (300 MHz, CDCl$_3$, δ ppm): 5.35 (bs, 1H), 4.45 (dd, j=8.3, 3.2 Hz, 1H), 4.24-4.37 (m, 2H), 4.06-4.13 (m, 2H), 3.72-3.98 (m, 3H), 2.46-2.47 (m, 1H), 1.23-2.04 (m, 24H).

Example 6: Synthesis of Compound of Formula (9a)

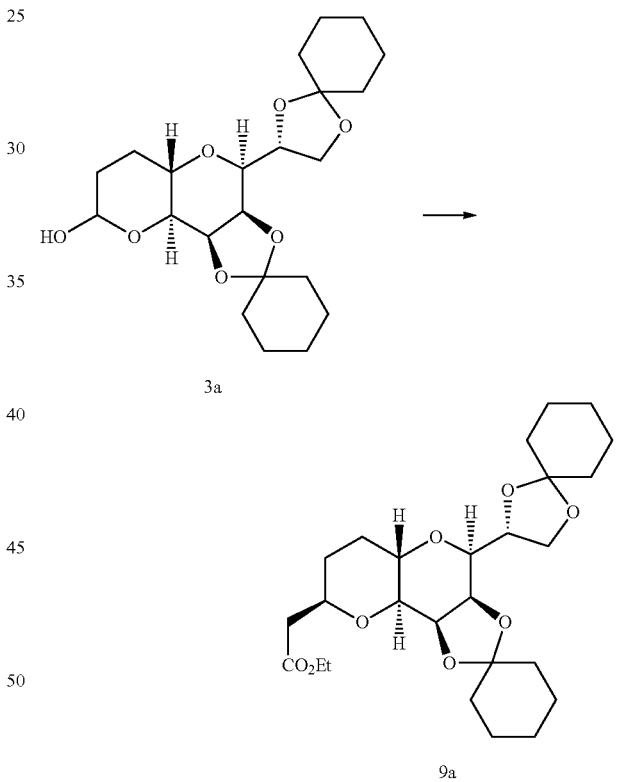

Triethyl phosphonoacetate (19 mL) was added to tetrahydrofuran (16 mL) and cooled to 0° C. or lower. Potassium tert-butoxide (10.3 g) was added thereto, followed by stirring for about 30 minutes. The compound of formula (3a) (15.7 g) dissolved in tetrahydrofuran (16 mL) was added thereto, followed by stirring for 15 hours at room temperature. After the completion of the reaction was confirmed, saturated ammonium chloride aqueous solution (200 mL) was added thereto, and the resulting solution was strongly stirred. After the organic layer was separated, the aqueous layer was extracted with ethyl acetate. Sodium sulfate was added to the combined organic layer, followed by filtration and concentration. The resulting residue was subjected to chromatography (ethyl acetate:n-hexane=1:3) to give the compound of formula (9a) (14.6 g, 79.4%).

¹H NMR (300 MHz, CDCl₃, δ ppm): 4.52 (dd, J=2.9 Hz, 1H), 4.22-4.34 (m, 2H), 4.06-4.17 (m, 3H), 3.76-3.95 (m, 3H), 3.72 (dd, J=7.1, 1.5 Hz, 1H), 3.49 (dd, J=10.2, 3.0 Hz, 1H), 2.70 (dd, J=16.0, 6.8 Hz, 1H), 2.41 (dd, J=16.0, 6.2 Hz, 1H), 2.13-2.20 (m, 1H), 1.22-1.84 (m, 26H).

Example 7: Synthesis of Compound of Formula (10a)

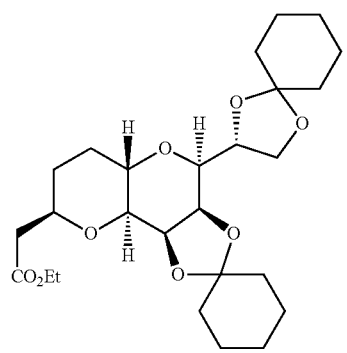

9a

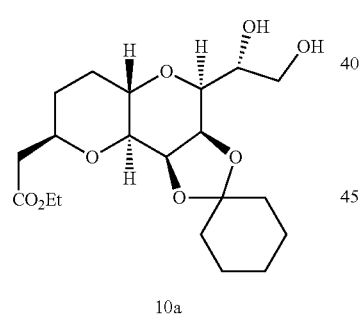

10a

To the compound of formula (9a) (32 g) was added acetic acid:water=4:1 (640 mL), followed by stirring for about 7 hours at the temperature of 30-35° C. After the completion of the reaction was confirmed, toluene (640 mL) was added, followed by concentration under reduced pressure. The resulting residue was subjected to chromatography (methylene chloride:methanol=10:1) to give the compound of formula (10a) (23 g, 86.3%).

¹H NMR (300 MHz, CDCl₃, δ ppm): 4.56 (dd, J=8.4, 2.9 Hz, 1H) 4.45 (dd, J=8.4, 1.4 Hz, 1H), 4.13 (q, J=71 Hz, 2H), 3.82-3.95 (m, 3H), 3.75-3.81 (m, 3H), 3.51 (dd, J=10.2, 2.9 Hz, 1H), 3.15 (bs, 1H), 2.70 (dd, J=16.0, 6.8 Hz, 1H), 2.38-2.45 (m, 2H), 2.08-2.14 (m, 1H), 1.22-1.84 (m, 16H),

Example 8: Synthesis of Compound of Formula (11a)

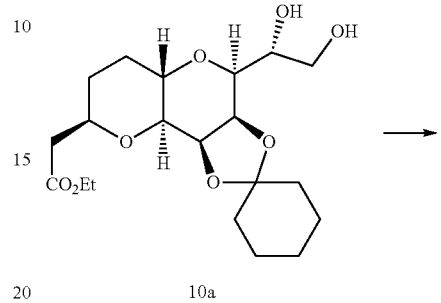

10a

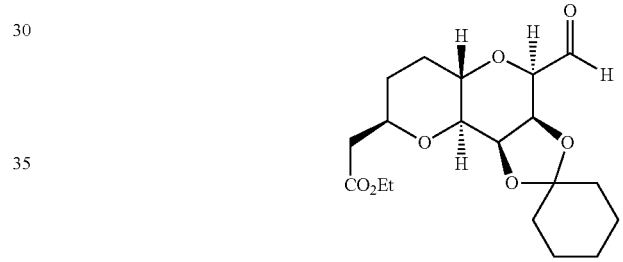

11a

The compound of formula (10a) (23 g) was dissolved in ethyl acetate (230 mL) and water (230 mL), and cooled to 0° C. Sodium periodate (12.9 g) was added thereto with maintaining the temperature of 10° C. or lower, followed by stirring for about 2 hours at room temperature. After the completion of the reaction was confirmed, sodium chloride (23 g) was added thereto, followed by stirring for 30 minutes. After the resulting by-products were filtered, the organic layer was separated and the aqueous layer was extracted three times with ethyl acetate (115 mL). The combined organic layer was washed with 20% sodium chloride aqueous solution (115 mL). Sodium sulfate was added to the organic layer, followed by filtration and concentration, and the obtained compound of formula (11a) (20 g, 94.5%) was used for the following reaction without additional purification.

¹H NMR (300 MHz, CDCl₃, δ ppm): 9.62 (d, J=0.6 Hz, 1H), 4.70 (dd, J=8.2, 2.2 Hz, 1H), 4.58 (dd, J=8.2, 3.0 Hz, 1H), 4.10-4.17 (m, 31H), 3.96-4.05 (m, 1H), 3.82-3.90 (m, 1H), 3.43 (dd, J=7.1 Hz, 2H), 3.82-3.90 (m, 1H), 3.43 (dd, J=10.2, 3.0 Hz, 1H), 2.71 (dd, J=16.1, 6.9 Hz, 1H), 2.42 (dd, J=16.1, 6.1 Hz, 1H), 2.18-2.25 (m, 1H), 1.23-1.83 (m, 16H).

Example 9: Synthesis of Compound of Formula (12a)

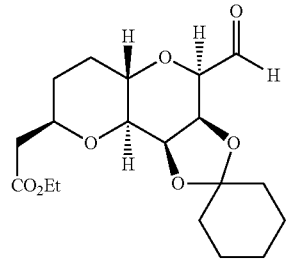

11a

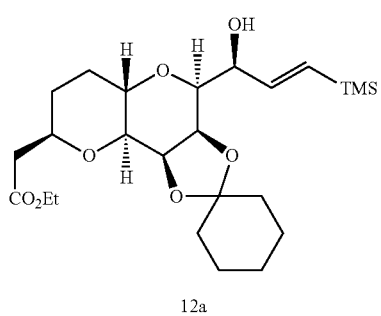

12a

Chromium(II) chloride (100 g) and nickel(II) chloride (1.06 g) were added to dimethylsulfoxide (210 mL) and acetonitrile (210 mL), and cooled to 0-5° C. The compound of formula (11a) (30 g) and (2-bromovinyl)trimethylsilane (73 mL) were dissolved in acetonitrile (210 mL) and added dropwise. The resulting solution was stirred for 24 hours at room temperature and the completion of the reaction was confirmed. Methanol (200 mL), water (200 mL), MTBE (200 mL) were added thereto, followed by stirring for 1 hour. The organic layer was separated, and the aqueous layer was extracted twice with MTBE (100 mL). The combined organic layer was washed with saturated sodium chloride (200 mL), and sodium sulfate was added to the organic layer, followed by filtration and concentration. The resulting residue was subjected to chromatography (ethyl acetate:n-hexane=1:2) to give a compound of formula (12a) (18.2 g, 48%).

$^1$H NMR (300 MHz, CDCl$_3$, δ ppm): 6.06-6.19 (m, 2H), 4.47-4.55 (m, 2H), 4.32-4.38 (m, 1H), 4.14 (q, J=7.1 Hz, 2H), 3.80-3.98 (m, 2H) 3.63 (dd, J=5.2, 1.1 Hz, 1H), 3.49 (dd, J=1.02, 2.7 Hz, 1H), 3.02 (d, J=7.7 Hz, 1H), 2.70 (dd, J=16.0, 6.8 Hz, 1H), 2.41 (dd, J=16.0, 6.2 Hz, 1H), 2.08-2.18 (m, 1H), 1.17-1.81 (m, 16H), 0.08 (s, 9H).

Example 10: Synthesis of Compound of Formula (13)

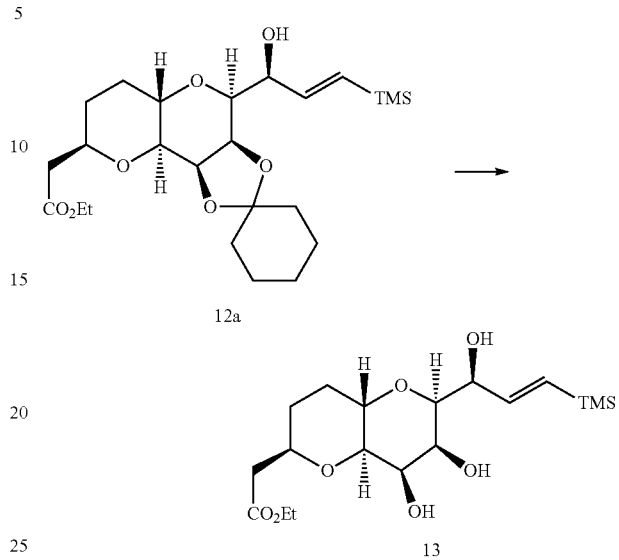

To the compound of formula (12a) (18.2 g) was added acetic acid:water=1:1 (149 mL), followed by stirring for about 3 hours at the temperature of 90-95° C. After the completion of the reaction was confirmed, the resulting solution was cooled to 15° C. or lower, and washed twice with heptane (73 mL). 20% Potassium hydrogen carbonate (700 mL) and MTBE (146 mL) were added to the aqueous layer. The organic layer was separated, and washed with 5% potassium hydrogen carbonate (75 mL) and 5% sodium chloride (75 mL). The organic layer was concentrated, and MTBE (60 mL) was added thereto, followed by warming to 55° C. for dissolution. Heptane (145 mL) was added dropwise thereto, with maintaining the temperature exceeding 40° C. The resulting solution was cooled to 5-15° C. and stirred for 15 hours. The resulting solution was filtered with heptane to give a compound of formula (13) (10.1 g, 67%).

$^1$H NMR (300 MHz, CDCl$_3$, δ ppm): 6.14 (dd, J=18.7, 5.9 Hz, 1H), 5.97 (dd, J=18.7, 0.9 Hz, 1H), 5.04-5.10 (m, 1H), 4.11-4.27 (m, 4H), 3.98-4.03 (m, 1H), 3.87-3.91 (m, 1H), 3.76 (dd, J=8.8, 6.2 Hz, 1H), 3.54-3.57 (m, 1H), 3.22 (d, J=3.2 Hz, 1H), 2.94 (bs, 1H), 2.59 (dd, J=15.4, 7.4 Hz, 1H), 2.42 (dd, J=15.4, 5.5 Hz, 1H), 1.90-1.93 (m, 1H), 1.80-1.82 (m, 1H) 1.39-1.46 (m, 2H), 1.26 (t, J=7.1 Hz, 3H), 0.07 (s, 9H).

Example 11: Synthesis of Compound of Formula (14)

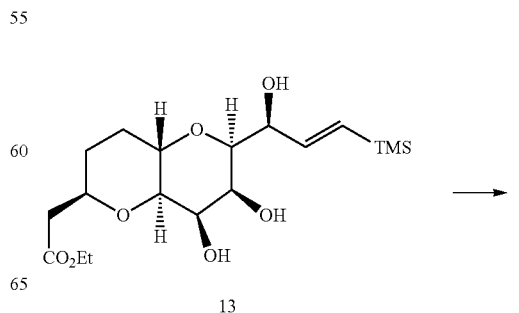

13

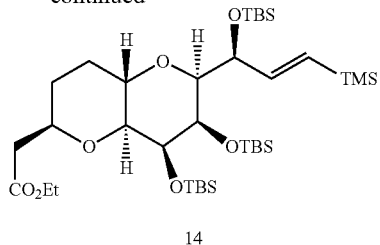

14

To the compound of formula (13) (5 g) was added MTBE (37.4 mL), and 2,6-lutidine (11.1 mL) was added thereto for dissolution, followed by cooling to 0° C. t-Butyldimethylsilyl trifluoromethanesulfonate (10.3 mL) was added thereto, followed by stirring for about 24 hours at room temperature. After the completion of the reaction was confirmed, methanol (1.3 mL) and water (74.7 mL) were added dropwise thereto. The organic layer was separated and washed twice with 1N hydrochloric acid (80 mL), 5% sodium chloride (75 mL), 5% sodium bicarbonate (75 mL), and 5% sodium chloride (75 mL). The organic layer was concentrated under reduced pressure, and the resulting residue was subjected to chromatography (ethyl acetate:n-hexane=1:10) to give a compound of formula (14) (7.2 g, 76.5%).

$^1$H NMR (300 MHz, CDCl$_3$, δ ppm): 6.13 (dd, J=18.9, 8.0 Hz, 1H), 5.81 (dd, J=18.9, 0.5 Hz, 1H), 4.92-4.96 (m, 1H), 4.02-4.11 (m, 3H), 3.69-3.84 (m, 3H), 3.39-3.47 (m, 1H), 3.85 (dd, J=9.6, 2.3 Hz, 1H), 2.45 (dd, J=15.3, 8.0 Hz, 1H), 2.27 (dd, J=15.3, 5.3 Hz, 1H), 1.64-1.71 (m, 2H), 1.16-1.21 (m, 5H), 0.90 (s, 9H), 0.86 (s, 9H), 0.78 (s, 9H), −0.09-0.05 (s, 27H).

Example 12: Synthesis of Compound of Formula (15)

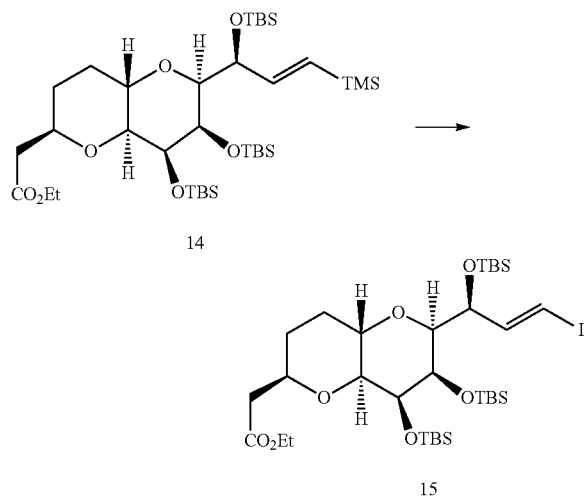

The compound of formula (14) (7.1 g) was dissolved in toluene (18.5 mL), and acetonitrile (33.4 mL) was added thereto. t-Butyldimethylsilyl chloride (73 mg) was added thereto, followed by warming to 30° C. N-Iodosuccinimide (8.74 g) was added thereto, and stirred for about 24 hours. After the completion of the reaction was confirmed, the resulting solution was cooled to 25° C. or lower, and a mixture of 5% sodium hydrogen carbonate aqueous solution (35.5 mL) and 5% sodium thiosulfate aqueous solution (35.5 L) was added thereto, followed by stirring for 30 minutes. The organic layer was separated, and the aqueous layer was extracted with ethyl acetate. The combined organic layer washed twice with 10% sodium chloride (70 mL), and sodium sulfate was added to the organic layer, followed by filtration and concentration. The resulting residue was subjected to chromatography (ethyl acetate:n-hexane=1:10) to give a compound of formula (15) (6.7 g, 87.2%).

$^1$H NMR (300 MHz, CDCl$_3$, δ ppm): 6.86 (dd, J=14.6, 7.8 Hz, 1H), 6.28 (dd, J=14.6, 0.7 Hz, 1H), 4.88-4.92 (m, 1H), 4.07-4.21 (m, 3H), 3.77-3.90 (m, 3H), 3.42-3.51 (m, 1H), 2.93 (dd, J=9.6, 2.2 Hz, 1H), 2.53 (dd, J=15.4, 8.1 Hz, 1H), 2.36 (dd, J=15.4, 5.1 Hz, 1H), 1.92-1.97 (m, 1H), 1.70-1.82 (m, 1H), 1.23-1.28 (m, 3H), 0.94 (s, 9H), 0.92 (s, 9H), 0.86 (s, 9H), 0.02-0.11 (s, 18H).

Example 13: Synthesis of Compound of Formula (2)

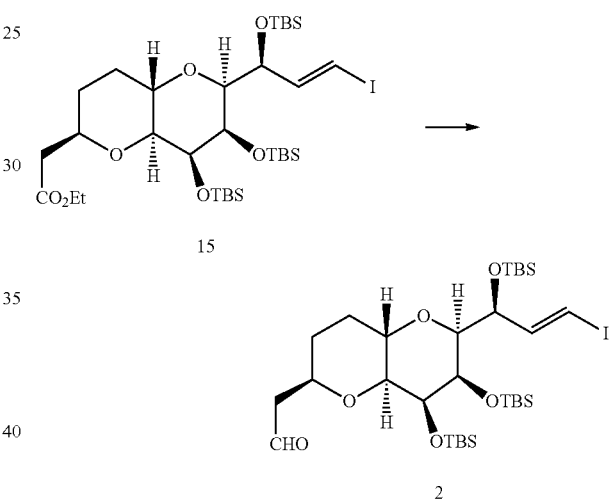

The compound of formula (15) (1 g) was dissolved in toluene (14 mL), and cooled to −65° C. or lower. 1.2 M DIBAL-H (1.4 mL) was added dropwise thereto with maintaining the temperature of −60° C. or lower, and stirred for 30 minutes, followed by confirming the completion of the reaction. Methanol (0.15 mL) was added dropwise thereto, and 1N hydrochloric acid (10 mL) and MTBE (4 mL) were added thereto, followed by stirring for 30 minutes. The organic layer was separated, and washed with 1 N hydrochloric acid (10 mL), water (10 mL), saturated sodium bicarbonate (10 mL), and saturated sodium chloride (10 mL). Sodium sulfate was added to the organic layer, followed by filtration and concentration under reduced pressure. The resulting residue was subjected to chromatography (ethyl acetate:n-hexane=1:8) to give a compound of formula (2) (890 mg, 94.6%).

$^1$H NMR (300 MHz, CDCl$_3$, δ ppm): 9.78-9.79 (m, 1H), 6.85 (dd, J=14.6, 7.9 Hz, 1H), 6.29 (dd, J=14.6, 0.7 Hz, 1H), 4.88-4.92 (m, 1H), 4.08-4.11 (m, 1H), 3.81-3.93 (m, 3H), 3.45-3.53 (m, 1H), 2.95 (dd, J=9.6, 2.3 Hz, 1H), 2.63 (ddd, J=16.5, 8.5, 2.6 Hz, 1H), 2.44 (ddd, J=16.4, 4.4, 1.7 Hz, 1H), 1.95-1.98 (m, 1H), 1.74-1.79 (m, 1H), 1.32-1.46 (m, 2H), 0.94 (s, 9H), 0.93 (s, 9H), 0.86 (s, 9H), 0.02-0.11 (s, 18H).

The invention claimed is:

1. A process for preparing a compound of the following formula (3), which comprises the steps of:
    subjecting a compound of the following formula (4) to Wittig reaction to obtain a compound of the following formula (5);
    (ii) selectively deprotecting a $PG_2$ group of the compound of the following formula (5) to obtain a compound of the following formula (6);
    (iii) subjecting the compound of the following formula (6) to cyclization to obtain a compound of the following formula (7);
    (iv) subjecting the compound of the following formula (7) to hydrogenation to obtain a compound of the following formula (8); and
    (v) reducing an ester group of the compound of the following formula (8):

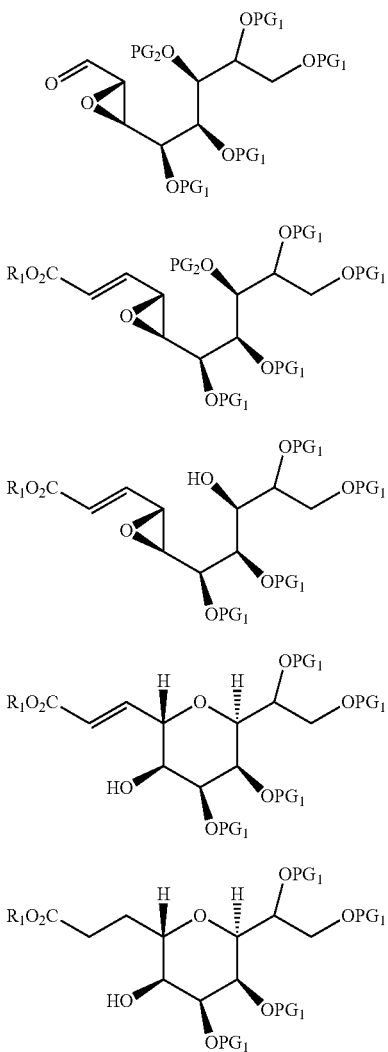

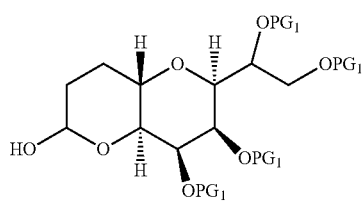

wherein, $PG_1$ represents a diol protecting group forming a 5-membered heterocycle by combining each other, and is derived from cyclopentanone, cyclohexanone, cycloheptanone, 1,1-dimethoxycyclopentane, 1,1-dimethoxycyclohexane or 1,1-dimethoxycycloheptane, $PG_2$ represents a silyl protecting group, and $R_1$ represents hydrogen or a $C_1$-$C_6$ alkyl group.

2. The process according to claim 1, wherein the Wittig reaction of step (i) is carried out using (methoxycarbonylmethylene)triphenylphosphorane or (ethoxycarbonylmethylene)triphenylphosphorane.

3. The process according to claim 1, wherein the deprotection of step (ii) is carried out using a mixture of a fluoride compound and a buffer.

4. The process according to claim 3, wherein the buffer is imidazole hydrochloride.

5. The process according to claim 1, wherein the cyclization of step (iii) is carried out in the presence of a catalyst.

6. The process according to claim 5, wherein the catalyst is di-μ-chloro-tetracarbonyldirhodium(I).

7. The process according to claim 1, wherein the hydrogenation of step (iv) is carried out in the presence of Pd/C.

8. The process according to claim 1, wherein the reduction of step (v) is carried out using diisobutylaluminum hydride.

9. A compound of the following formula (3):

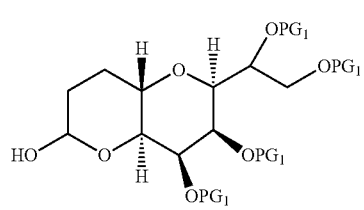

wherein, $PG_1$ represents a diol protecting group forming a 5-membered heterocycle by combining each other, and is derived from cyclopentanone, cyclohexanone, cycloheptanone, 1,1-dimethoxycyclopentane, 1,1-dimethoxycyclohexane or 1,1-dimethoxycycloheptane.

* * * * *